United States Patent
Payne et al.

(10) Patent No.: US 7,993,633 B2
(45) Date of Patent: Aug. 9, 2011

(54) CYCLOHEXYLETHYL CARBOXYLIC ACID ESTER COMPOSITIONS AND METHOD FOR USING THE SAME FOR REDUCING MALODORS

(75) Inventors: Richard K. Payne, Brielle, NJ (US); Richard M. Boden, Ocean, NJ (US); Mónica Díaz Sierra, Castellon (ES); Matthias H. Tabert, Arverne, NY (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 12/504,204

(22) Filed: Jul. 16, 2009

(65) Prior Publication Data

US 2011/0014142 A1    Jan. 20, 2011

(51) Int. Cl.
*A01N 1/00* (2006.01)
(52) U.S. Cl. ......................................... 424/75
(58) Field of Classification Search ....... 424/75
See application file for complete search history.

(56) References Cited

U.S. PATENT DOCUMENTS

| | | | |
|---|---|---|---|
| 4,534,891 A | | 8/1985 | Boden et al. |
| 4,622,221 A | * | 11/1986 | Schleppnik ............... 424/76.4 |
| 6,432,891 B1 | | 8/2002 | O'Connor |
| 6,592,813 B1 | | 7/2003 | Fox et al. |
| 2004/0156742 A1 | | 8/2004 | Milan et al. |
| 2005/0106192 A1 | * | 5/2005 | Parekh et al. ............... 424/401 |
| 2009/0067760 A1 | | 3/2009 | Shelley et al. |

OTHER PUBLICATIONS

Ema et al., Chemical Communications (Cambridge, United Kingdom) 37: 4650-4651 (2005).*
Verzijl et al., Tetrahedron Assymetry 16: 1603 (2005).*
Li, G et al. "Application of 1,2:5,6-di-O-cyclohexylidene-D-mannitol as the chiral director in Matteson's asymmetric homologation" J Organometallic Chem 581 (1999) 66-69.
Sokeirik, Y.S. et al. "Synthesis of a fluorous ligand and its application for asymmetric addition of dimethylzinc to aldehydes" Organic Lett 9(10) (2007) 1927-1929.
European Search Report.

* cited by examiner

*Primary Examiner* — James H Alstrum Acevedo
*Assistant Examiner* — Thor Nielsen
(74) *Attorney, Agent, or Firm* — Elizabeth M. Quirk; XuFan Tseng; Joseph F. Leightner

(57) ABSTRACT

The present invention pertains to a method of counteracting a malodor by introducing a malodor counteracting effective amount of an enantiomeric compound selected from the group consisting of (1R)-1-cyclohexylethyl butyrate and (1S)-1-cyclohexylethyl acetate.

2 Claims, No Drawings

US 7,993,633 B2

CYCLOHEXYLETHYL CARBOXYLIC ACID ESTER COMPOSITIONS AND METHOD FOR USING THE SAME FOR REDUCING MALODORS

FIELD OF THE INVENTION

The present invention relates to novel compositions and methods for counteracting malodors.

BACKGROUND OF THE INVENTION

"Malodor" is a term used to describe undesirable or unpleasant odor. Common sources of malodors include body perspiration, smoke, environmental odor such as mold and mildew, bathroom, and etc. Numerous methods have been developed to prevent or reduce malodors in a variety of circumstances. For example, conventional perfumes including a variety of fragrance materials are developed to mask malodors, which generally function via two mechanisms: first, the fragrance materials blend with the malodor compound to provide a different and more desirable aroma; and second, the fragrance materials are employed in a large quantity to overwhelm the malodor compound.

Additionally, certain cyclohexylethyl carboxylic acid ester compounds (VEILEX™, commercially available from International Flavors & Fragrances Inc.) may bind to the same receptors in the nose as the malodor molecules, thereby counteract the perception of malodors by rendering these receptors unavailable to malodor molecules. The combination use of VEILEX™ compounds such as 1-cyclohexylethyl butyrate ("VEILEX™ 1"), 1-cyclohexylethyl acetate ("VEILEX™ 2"), and 1-cyclohexylethanol ("VEILEX™3") for suppressing a range of malodors is disclosed in U.S. Pat. Nos. 4,622, 221, 6,432,891, and 6,592,813, and published U.S. patent application 2005/0106192.

However, none of the above malodor counteracting methods provides malodor-specific effect. Consequently, to eliminate the perception of a particular malodor effectively, a high amount of malodor counteracting compositions is often required. Thus, there is a need in the art to provide a malodor-specific counteractant composition that can be effective at a low amount.

Nothing in the art discloses the effect of any of the aforementioned VEILEX™ compounds against a specific malodor.

SUMMARY OF THE INVENTION

The present invention provides a method for counteracting malodors using enantiomeric cyclohexylethyl carboxylic acid ester compounds.

Specifically, the present invention is directed to the enantiomeric compounds (1R)-1-cyclohexylethyl butyrate ("VEILEX™ 1R") and (1S)-1-cyclohexylethyl acetate ("VEILEX™ 2S"), which are represented by formulas set forth below:

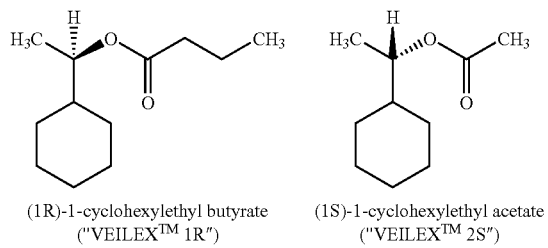

(1R)-1-cyclohexylethyl butyrate ("VEILEX™ 1R")

(1S)-1-cyclohexylethyl acetate ("VEILEX™ 2S")

The present invention is also directed to the surprising finding of the unexpected effectiveness of a (1R)-1-cyclohexylethyl butyrate-containing composition in counteracting mold/mildew malodor.

The present invention is also directed to the surprising finding of the unexpected effectiveness of a (1S)-1-cyclohexylethyl acetate-containing composition in counteracting sweat malodor.

These and other embodiments of the present invention will be apparent by reading the following specification.

DETAILED DESCRIPTION OF THE INVENTION

The racemic cyclohexylethyl carboxylic acid ester compounds such as VEILEX™ I, VEILEX™ II, and VEILEX™ III are known in the art. Mixtures of their racemic compounds have been developed in counteracting a range of malodors. However, there is no disclosure of the effect of an individual compound against specific malodors.

Further, the activities of many compounds are often associated with their chiral configuration. A compound of a wrong enantiomeric form may lack desirable biological, physical or chemical properties. However, identifying a chiral center and developing a cost-effective process to synthesize enantiomers and/or targeted racemic compounds pose difficult challenges, let alone discovering an active form is unpredictable as such effort may often not lead to a desirable enantiomer that possesses stronger function than the others and/or its racemate. No disclosure is made of the optical activities of any of the cyclohexylethyl carboxylic acid ester compounds, let alone their respective malodor counteracting effects.

The present invention discloses enantiomeric cyclohexylethyl carboxylic acid ester compounds of the following:

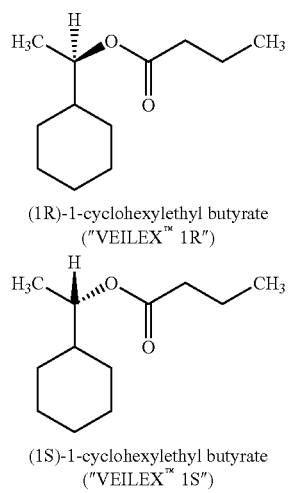

(1R)-1-cyclohexylethyl butyrate ("VEILEX™ 1R")

(1S)-1-cyclohexylethyl butyrate ("VEILEX™ 1S")

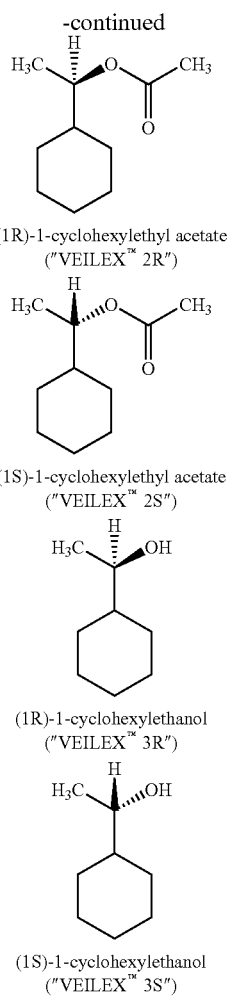

(1R)-1-cyclohexylethyl acetate
("VEILEX™ 2R")

(1S)-1-cyclohexylethyl acetate
("VEILEX™ 2S")

(1R)-1-cyclohexylethanol
("VEILEX™ 3R")

(1S)-1-cyclohexylethanol
("VEILEX™ 3S")

It has been surprisingly discovered that the above enantiomeric compounds selectively target different types of malodors such as body perspiration, environmental odor such as mold and mildew, bathroom, and etc. Particularly, (1R)-1-cyclohexylethyl butyrate is distinctly effective in counteracting mold/mildew malodor and (1S)-1-cyclohexylethyl acetate is distinctly effective in counteracting sweat malodor. Thus, when compared to previously known racemates and other enantiomers identified herein, (1R)-1-cyclohexylethyl butyrate and (1S)-1-cyclohexylethyl acetate provide superior ingredient performance and possess unexpected advantages in specific malodor counteracting applications.

Accordingly, one embodiment of the present invention relates to a method for counteracting a malodor by introducing a malodor counteracting effective amount of an enantiomeric cyclohexylethyl carboxylic acid ester compound into air space wherein the malodor is present or a substrate on which the malodor has deposited.

Another embodiment of the present invention relates to a method for counteracting a mold/mildew malodor by introducing a malodor counteracting effective amount of (1R)-1-cyclohexylethyl butyrate into air space wherein the malodor is present or a substrate on which the malodor has deposited.

Another embodiment of the present invention relates to a method for counteracting a sweat malodor by introducing a malodor counteracting effective amount of (1S)-1-cyclohexylethyl acetate into air space wherein the malodor is present or a substrate on which the malodor has deposited.

As stated above, the enantiomeric compounds of the present invention substantially eliminate the perception of specific malodors of mold/mildew and sweat, and/or prevent the formation of such malodors while simultaneously refraining from reduction of the perception of pleasant fragrance aromas. The enantiomeric compounds of the present invention can be utilized with a vast number of functional products.

Examples of the functional products are provided herein to illustrate the various aspects of the present invention. However, they do not intend to limit the scope of the present invention. The functional products may include, for example, a conventional room freshener (or deodorant) composition such as room freshener sprays, an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towellets, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulphide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processings, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, and subways and transport systems.

Thus, it will be seen that the composition of the invention is usually one in which the malodor counteractant is present together with a carrier by means of which or from which the malodor counteractant can be introduced into air space wherein the malodor is present, or a substrate on which the malodor has deposited. For example, the carrier can be an aerosol propellant such as a chlorofluoro-methane, or a solid such as a wax, plastics material, rubber, inert powder or gel. In a wick-type air freshener, the carrier is a substantially odorless liquid of low volatility. In several applications, a composition of the invention contains a surface active agent or a disinfectant, while in others, the malodor counteractant is present on a fibrous substrate. In many compositions of the invention there is also present a fragrance component which imparts a fragrance to the composition. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like.

Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Malodor counteracting effective amount is understood to mean the amount of the inventive malodor counteractant employed in a functional product that is organoleptically effective to abate a given malodor while reducing the combined intensity of the odor level, wherein the given malodor is present in air space or has deposited on a substrate. The exact amount of malodor counteractant agent employed may vary depending upon the type of malodor counteractant, the type of the carrier employed, and the level of malodor counteractancy desired. In general, the amount of malodor counteractant agent present is the ordinary dosage required to obtain the desired result. Such dosage is known to the skilled practitioner in the art. In a preferred embodiment, when used in conjunction with malodorous solid or liquid functional products, e.g., soap and detergent, the enantiomeric compound-containing composition of the present invention may be present in an amount ranging from about 0.0001% to about 10%, preferably from about 0.001% to about 5%, and more preferably from about 0.01% to about 2%, by weight; and when used in conjunction with malodorous gaseous functional products, the enantiomeric compound-containing composition of the present invention may be present in an amount ranging from about 0.01 to 1 mg per cubic meter of air.

The compounds of the present invention may be prepared via a general scheme depicted as follows:

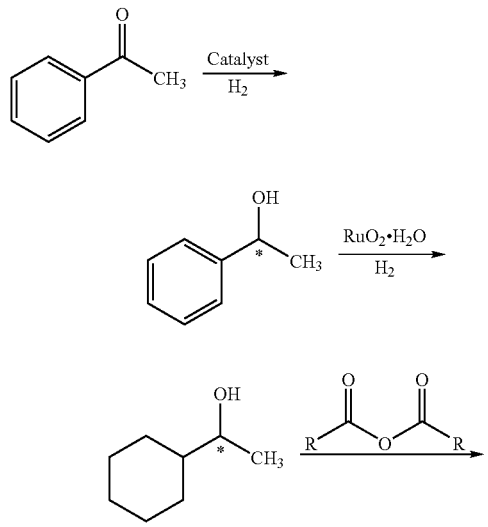

-continued

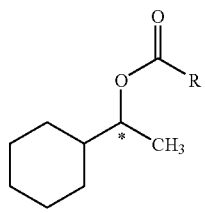

wherein * indicates a chiral center;

"catalyst" represents R-XylPPhos RuCl$_2$ R-DAIPEN or S-XylPPhos RuCl$_2$ S-DAIPEN, which provides a corresponding chiral alcohol; and "R" represents a methyl or propyl group.

The following are provided as specific embodiments of the present invention. Other modifications of this invention will be readily apparent to those skilled in the art. Such modifications are understood to be within the scope of this invention. All reaction reagents were purchased from Sigma-Aldrich Inc. As used herein all percentages are weight percent unless otherwise noted, ee is understood to be enantiomeric excess, mmHg is understood to be millimeters of mercury, M is understood to be moles per Liter, ppm is understood to stand for parts per million, L is understood to be liter, mL is understood to be milliliter, Kg is understood to be kilogram, g be gram, and mg be milligram. IFF as used in the examples is understood to mean International Flavors & Fragrances Inc., New York, N.Y., USA.

EXAMPLE I

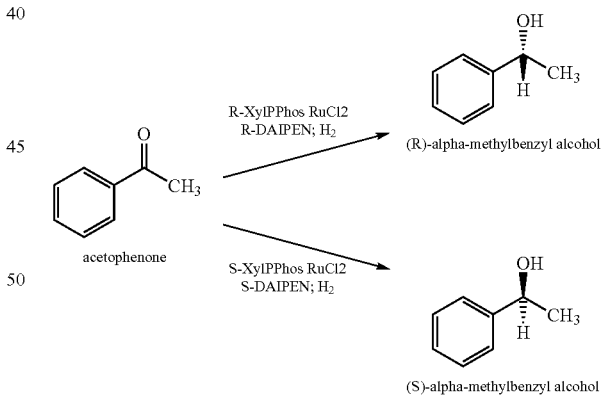

Preparation of (R)- and (S)-alpha-methylbenzyl alcohol: An autoclave was charged with acetophenone (1.03 Kg), isopropanol (300 g), and KOH (100 g, 10 M). Catalyst R-XylPPhos RuCl$_2$ R-DAIPEN (150 mg) was then added, and the reaction mixture was hydrogenated at a pressure of 30 bar and a temperature of 70° C. for 12 hours. The resultant mixture was transferred into a separatory funnel. The aqueous layer was discarded. The organic layer was washed with water (200 ml) and distilled first at 100 mmHg to remove isopropanol, and then at 5-10 mmHg to provide (R)-alpha-methylbenzyl alcohol (980 g).

The same process was carried out using S-XylPPhos RuCl₂ S-DAIPEN (150 g) as the catalyst to provide (S)-alpha-methylbenzyl alcohol in the same yield (980 g).

EXAMPLE II

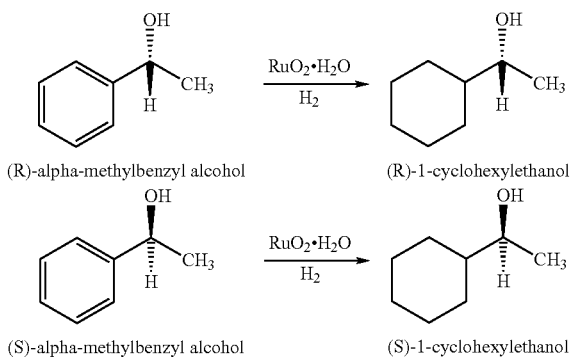

(R)-alpha-methylbenzyl alcohol → (R)-1-cyclohexylethanol (S)-alpha-methylbenzyl alcohol → (S)-1-cyclohexylethanol Preparation of (R)- and (S)-1-cyclohexylethanol: An autoclave was charged with (R)-alpha-methylbenzyl alcohol (980 g, synthesized as above) and isopropanol (100 g). Catalyst RuO₂.H₂O (0.2 g) was then added, and the reaction mixture was hydrogenated at a pressure of 20 bar and a temperature ranging from 70 to 80° C. for 4 hours. The catalyst was filtered. The organic layer was distilled first at 100 mmHg to remove isopropanol, and then at 5-10 mmHg to provide (R)-1-cyclohexylethanol (913 g) (optical rotation: $[\alpha]_D$ −4.31°; optical purity: 83.3% ee).

The same process was carried out using (S)-alpha-methylbenzyl alcohol (980 g, synthesized as above) as the starting material to provide (S)-1-cyclohexylethanol in the same yield (913 g) (optical rotation: $[\alpha]_D$ +4.46°; optical purity: 81.6% ee).

The product (R)- and (S)-1-cyclohexylethanol have the following NMR spectral characteristics: 0.9-1.1 ppm (m, 2H); 1.2-1.32 ppm (m, 3H); 1.5 ppm (d, 3H); 1.6-1.85 ppm (m, 6H); 3.65 ppm (q, 1H).

EXAMPLE III

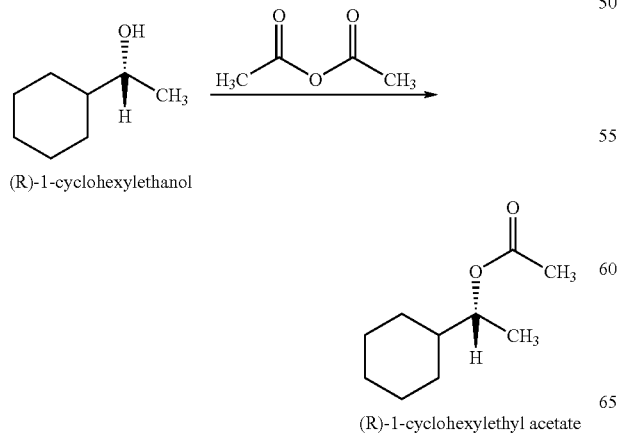

(R)-1-cyclohexylethanol (R)-1-cyclohexylethyl acetate

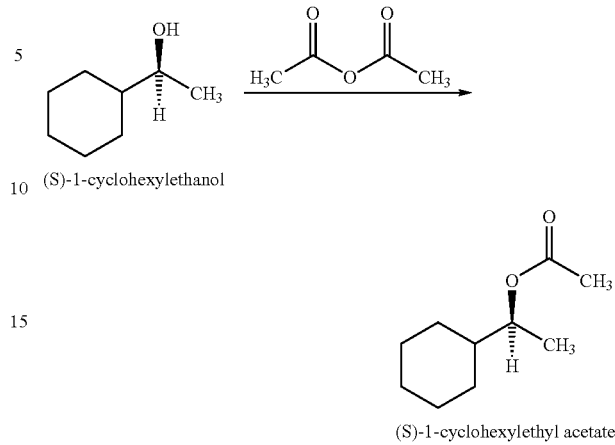

(S)-1-cyclohexylethanol (S)-1-cyclohexylethyl acetate

Preparation of (R)- and (S)-1-cyclohexylethyl acetate: A 2 L reaction flask was charged with (R)-1-cyclohexylethanol (980 g, synthesized as above), acetic anhydride (1 Kg), and p-toluene sulphonic acid (0.4 g), and heated at 30-40° C. for 6 hours. The reaction mixture was then transferred into a separatory funnel and washed twice in 200 mL water followed by once in 200 mL 10% sodium hydroxide (aOH). The resulted organic layer was distilled at 5-10 mmHg to provide (R)-1-cyclohexylethyl acetate (1.3 Kg) (optical rotation: $[\alpha]_D$ +2.59°; optical purity: 80.5% ee).

The same process was carried out using (S)-1-cyclohexylethanol (980 g, synthesized as above) as the starting material to provide (S)-1-cyclohexylethyl acetate in the same yield (1.3 Kg) (optical rotation: $[\alpha]_D$ −2.72°; optical purity: 85.5% ee).

The product (R)- and (S)-1-cyclohexylethyl acetate have the following NMR spectral characteristics:

0.9-1.1 ppm (m, 2H); 1.15 ppm (d, 3H); 1.1-1.3 ppm (m, 3H); 1.45-2.15 ppm (m, 9H); 2.15 ppm (d, 3H); 4.7 ppm (q, 1H).

EXAMPLE IV

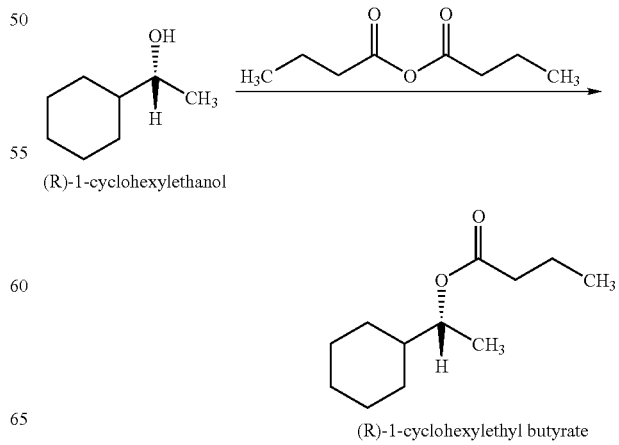

(R)-1-cyclohexylethanol (R)-1-cyclohexylethyl butyrate

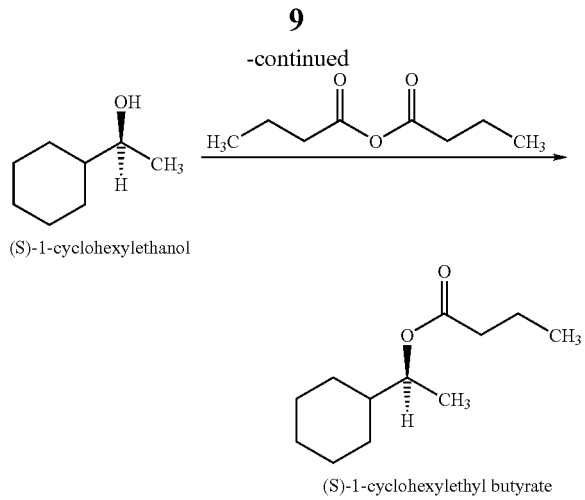

Preparation of (R)- and (S)-1-cyclohexylethyl butyrate: A 1 L reaction flask was charged with (R)-1-cyclohexylethanol (300 g, synthesized as above), butyric anhydride (600 g), and p-toluene sulphonic acid (0.4 g), and heated at 30-40° C. for 12 hours. The reaction mixture was then transferred into a separatory funnel and titrated with 20% NaOH to become basic followed by washing in 200 mL water. The resulted organic layer was distilled at 5-10 mmHg to provide (R)-1-cyclohexylethyl butyrate (402 g) (optical rotation: $[\alpha]_D$−0.11°; optical purity: 82.2% ee ).

The same process was carried out using (S)-1-cyclohexylethanol (300 g, synthesized as above) as the starting material to provide (S)-1-cyclohexylethyl butyrate in the same yield (402 g) (optical rotation: $[\alpha]_D$+1.02°; optical purity: 81.2% ee).

The product (R)- and (S)-1-cyclohexylethyl butyrate have the following NMR spectral characteristics:

0.9-1.05 ppm (m, 2H); 0.95 ppm (t, 3H); 1.1 ppm (d, 3H); 1.1-1.25 ppm (m, 3H); 1.4-1.8 ppm (m, 8H); 2.25 ppm (t, 2H); 4.7 ppm (q, 1H).

EXAMPLE V

Establishment of a Model of Sweat Malodor: It is known that the perspirative malodors of human body, particularly sweat, are associated with the production of several unpleasant smelling organic acids, particularly isovaleric acid ("IVA"). The commercial sample of this malodorous material (commercially available at Sigma-Aldrich Inc.) was thus used as a model compound to assess the effectiveness of sweat malodor counteractants.

Preparation of Test Samples: The VEILEX™ mixtures (VEILEX™ I, VEILEX™ II, and VEILEX™ III, commercially available from IFF) and the enantiomeric compounds of the present invention (all with optical purity over 80% ee, synthesized as above) were evaluated for sweat malodor counteracting effectiveness. Different concentrations of VEILEX™ mixtures and their enantiomeric counterparts were used based on priori usage levels. Additionally, the overall intensity of 1-cyclohexylethanol (1% in diethyl phthalate) was noticeably greater than the other two compounds, a higher concentration of IVA (2% in diethyl phthalate) was therefore used for the test.

Testing Procedure: A cyclohexylethyl carboxylic acid ester compound (1 g, a racemate or enantiomer) and IVA (1 g, 1-2%) were placed in two 1-ounce jars separately, which were both placed in a 1-gallon jar and capped for 24 hours to allow for the headspace saturation prior to the test. Each set of three test samples (i.e., three 1-gallone jars containing IVA and, respectively, a racemate and each of the two enantiomers) was presented in a blind, random order to internal panelists (consisting of trained females having a mean age of 40 years).

The panelists were instructed to take the steps of i) uncap a first jar; ii) place their noses immediately above the opening; iii) take short sniffs for 2-3 seconds; iv) cap the jar; v) repeat the steps after 30 seconds for the other two jars in the same set; and vi) provide a rank of the odor intensity for a set of three jars using the intensity scales of 1 to 5, where 1 represents the "Least Intense" and 5 represents the "Most Intense". The ranks of the odor intensity were then statistically analyzed using SPSS 15.0 for Windows. Freidman's non-parametric tests were used to analyze the ranked intensity for each test sample. Post hoc pair-wise comparisons were only conducted when the overall Chi-square omnibus test was statistically significant ($p<0.05$).

EXAMPLE V (CONT)

Results and Discussion: The mean ranks of the odor intensity for the above test were as follows (M=racemate; S=S enantiomer; and R=R enantiomer):

| Mal-odor | 1-cyclohexylethyl butyrate (5%) | | | 1-cyclohexylethyl acetate (2%) | | | 1-cyclohexylethanol (1%) | | |
|---|---|---|---|---|---|---|---|---|---|
| | M | S | R | M | S | R | M | S | R |
| IVA (1%) | 2.50 | 2.08 | 1.42 | 2.15 | 1.38* | 2.46 | — | — | — |
| IVA (2%) | — | — | — | — | — | — | 2.58 | 1.92 | 1.50 |

*Significant difference in the mean rank when compared to the corresponding racemate and R enantiomer.

Among all the compounds tested, only the S enantiomer of 1-cyclohexylethyl acetate (i.e., (1S)-1-cyclohexylethyl acetate) showed significant difference when compared with both racemate and the R enantiomer, which demonstrated that (1S)-1-cyclohexylethyl acetate is particularly effective in counteracting sweat malodor.

These results also indicate the discovery of a desirable enantiomeric cyclohexylethyl carboxylic acid ester compound, which possesses stronger function in counteracting a specific malodor than the corresponding racemate and/or enantiomer, is unpredictable.

EXAMPLE VI

Establishment of Mold/Mildew and Bathroom Malodor Models: In addition to the sweat model established as above, the malodor models of mold/mildew and bathroom were prepared based on applicant's proprietary formulations for assessing the effectiveness of mold/mildew and bathroom malodor counteractants.

Testing Procedure: The focus of this sensory testing was to directly compare the chiral enantiomers to each other for malodor coverage. Test samples were prepared the same as above. The same procedure was carried out except that a paired comparison test was used in which panelists were instructed to choose the sample from each chiral pair with the most intense malodor. Chi Square tests were used to analyze the frequency data in SPSS 15.0 for Windows.

Results and Discussion: Frequencies for each chiral pair tested, indicating the number of times a sample was chosen to be the most malodorous were as follows:

| Malodor | 1-cyclohexylethyl butyrate (5%) | | 1-cyclohexylethyl acetate (2%) | | 1-cyclohexylethanol (1%) | |
|---|---|---|---|---|---|---|
| | S | R | S | R | S | R |
| IVA (1%) | 8 | 4 | 2* | 11 | — | — |
| IVA (2%) | — | — | — | — | 7 | 5 |
| Mold/Mildew | 20 | 5* | 14 | 11 | 12 | 13 |
| Bathroom | 12 | 13 | 13 | 12 | 12 | 13 |

*Significant frequency differences when compared to the corresponding enantiomeric counterpart.

Among all the compounds tested, (1S)-1-cyclohexylethyl acetate was confirmed to be significantly and specifically effective in counteracting sweat malodor. It was also unexpectedly found that (1R)-1-cyclohexylethyl butyrate is significantly and specifically effective in counteracting mold/mildew malodor.

These results further confirm that the finding of a desirable enantiomer in counteracting a specific malodor is unpredictable.

What is claimed is:

1. A method of counteracting a malodor in air space or a substrate comprising the step of introducing a malodor counteractive effective amount of an enantiomeric compound, wherein the malodor is mold/mildew, and wherein the enantiomeric compound is (1R)-1-cyclohexylethyl butyrate, and wherein the malodor counteractive effective amount is about 5% by weight.

2. A method of counteracting a malodor in air space or a substrate comprising the step of introducing a malodor counteracting effective amount of an enantiomeric compound, wherein the malodor is sweat, and wherein the enantiomeric compound is (1S)-1-cyclohexylethyl acetate, and wherein the malodor counteracting effective amount is about 2% by weight.

* * * * *